United States Patent [19]

Dube

[11] 4,297,105
[45] Oct. 27, 1981

[54] AUTOMATIC PHOTOMETRIC TITRATOR

[75] Inventor: Ghyslain Dube, Arvida, Canada

[73] Assignee: Alcan Research and Development Limited, Montreal, Canada

[21] Appl. No.: 163,701

[22] Filed: Jun. 27, 1980

[51] Int. Cl.$^3$ .................. G01N 21/76; G01N 31/16
[52] U.S. Cl. .................................. 23/230 R; 422/52; 422/75; 250/361 C
[58] Field of Search .............. 23/230 R; 422/52, 75; 435/8; 250/361 C

[56] References Cited

U.S. PATENT DOCUMENTS 3,797,999 3/1974 Witz et al. .................... 422/52 X
4,220,450 9/1980 Maggio ........................... 435/8 X Primary Examiner—Ronald Serwin
Attorney, Agent, or Firm—Cooper, Dunham, Clark, Griffin & Moran

[57] ABSTRACT

An alkaline-acid end point detector for titration reactions in which the phenomenon of chemiluminescence is used to detect the end point by monitoring, by means of an electronic light detector, the light output of the reaction materials in a light-tight vessel. The output from the detector is differentiated to detect the maximum output which corresponds to the reaction end point. The detector is useful in the determination of acid numbers in oils and greases.

12 Claims, 3 Drawing Figures

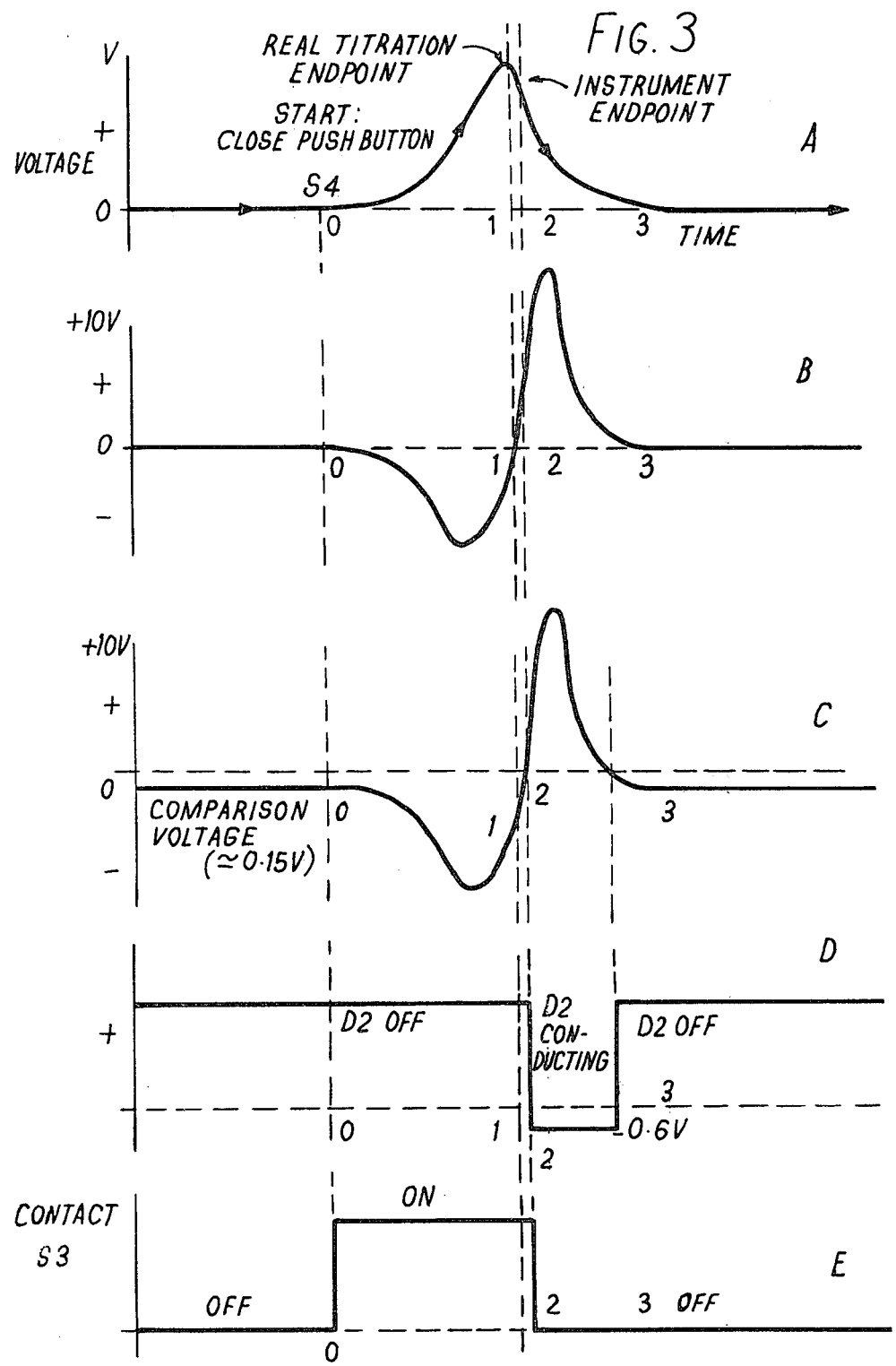

AUTOMATIC PHOTOMETRIC TITRATOR

This invention relates to an automatic photometric titrator, and in particular to a method and apparatus for detection of end-point in acid-base titration reactions. The invention finds particular, although not exclusive, use in the determination of acid numbers in a wide variety of oils and greases, including dark and opaque oils and greases which cannot be analysed by normal titration techniques.

The necessity of controlling, with accuracy and precision, the acid number levels in oil and grease, particularly in transformer oils and lubricants explain the many attempts made to develop a precise and rapid analytical technique and a semi or fully-automatic instrument for carrying it out. The basic principle of all titration reactions consists in neutralising the acidity of a sample being analysed by using a titrant consisting of a standard alkaline solution. The major difficulty is the detection of the end-point of the neutralisation, i.e. the point at which the sample turns from acidic to basic.

There are several known methods for the detection of end-point. For example, several methods are known in which a chemical indicator indicates by a colour change the end-point of the neutralisation. Such methods, however, are only useable in the analysis of colourless materials, giving substantially transparent solutions. These methods have also been found difficult to automate, and accuracy is poor.

Several other known methods are based on the known technique of potentiometric end-point detection using a hydrogen ion specific electrode. However, in addition to a dubious theoretical basis, such methods have been found difficult to use owing to several practical problems. For example, the equilibration for the electrode is very slow, and consequently it is impossible to carry out a titration in one continuous operation. Furthermore, since the end-point of the neutralisation is generally poorly defined, it can only be clearly revealed by executing the complete titration curve, point after point, each addition of titrant being followed by a waiting period of several minutes to allow the electrical potentials to equilibrate. Then the potential in mV is plotted against the quantity of base to obtain, by graphical determination, the end-point. Fifteen to thirty minutes for analysis is not unusual. In addition, the very low electrical conductivity of the solutions involved, and their non-aqueous nature, are responsible for electrical noise and electrode contamination problems.

The present invention seeks to reduce or avoid the problems of the known methods.

According to a first aspect of the present invention there is provided a method for detection of end-point in acid-base titration reactions, said method comprising placing a quantity of a chemiluminescent indicator together with a sample of the material to be analysed into a vessel, gradually adding a suitable titrant to the vessel whilst monitoring by means of a light detector the intensity of light emission from the indicator, obtaining the first derivative with respect to time of the output signal of the light detector and detecting when the first derivative of the output signal reaches an amplitude level indicative of the acid-base reaction end-point.

The phenomenon of chemiluminescence is exhibited by a small number of substances, and is the emission of light due to chemical reaction of the components of a system. For example, the compound lucigenin (N,N-dimethylnitrate acridinium) is capable of emitting light spontaneously when placed in contact with hydrogen peroxide ($H_2O_2$), which acts as a catalyser, and free hydroxide ions, which act as an activator. In fact, as will be shown below, the indicator cannot emit light unless an appreciable concentration of free hydroxide ions are available. The concentration of hydrogen peroxide can be adjusted to cope with samples having varying opacity—the darker the sample, the more hydrogen peroxide is needed for the same intensity of light emission.

Thus, the sample to be analysed (suitably solubilised or dispersed in an inert solvent) is mixed with the chemiluminescent indicator and hydrogen peroxide. The equation for the chemiluminescent reaction is given below:

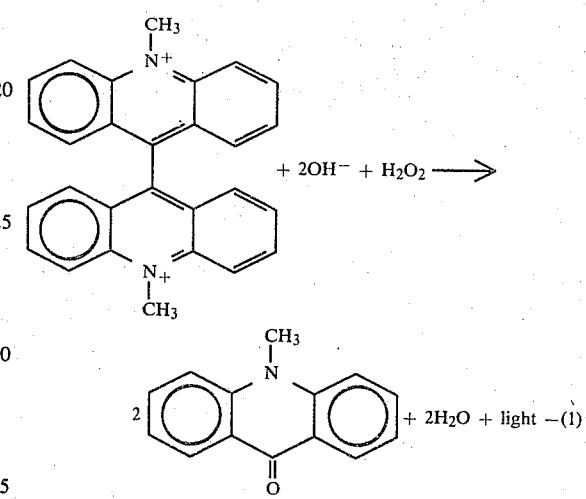

As titrant is added, the normal titration reaction carries on simultaneously with the chemiluminescent reaction. The equation for the titration reaction is given below:

$$A^-H^+ + OH^- \rightleftharpoons A^- + H_2O \qquad (2)$$

where AH represents the acid component of the material being analysed.

The titration reaction (2) has a stronger tendency to move to the right than the chemiluminescent reaction (1) so that, as free hydroxide ions ($OH^-$) are added in the form of titrant, these ions, initially at least, are used up by reaction (2) above, and only a small number are available for reaction (1). Hence the free hydroxide ions added will not, in the presence of the indicator, provide light emission. As reaction (2) proceeds, however, a steadily increasing number of free hydroxide ions become available for reaction (1) and the light emission thus gradually increases.

Tests have been carried out on various oils, and it is found that, if the oil contains a very strong acid (for example sulphuric acid), absolutely no light is emitted for a large proportion of the titration time. Then, as the $H^+$ concentration decreases, the concentration of free hydroxide ions starts to increase with simultaneous emission of light in accordance with reaction (1) above.

If the oil contains a weak acid then, irrespective of the concentration of the acid in the oil, a small but significant concentration of free hydroxide ions exists even at the beginning of the titration reaction and therefore, during titration, there is continuous competition between reactions (1) and (2), and the light emission will generally start at a very low intensity right at the beginning of titration and increase gradually and slowly during the entire titration.

It will be seen, therefore, that the manner in which the light intensity increases, prior to the end-point, is characteristic of the particular acid contained in the sample. Once the end-point is reached, however, the increase in light emission intensity is halted and thence starts to decrease. This reduction in light intensity after the neutral point is due to excess titrant, and observations have shown that the rate of decrease of light intensity does not change from sample to sample. The point of maximum light emission, which is very reliable, is used as a reference level, and any increase in the volume of standard KOH solution required to reach this particular reference level is attributable to an increase in the acidity level of the sample.

The phenomenon of chemiluminescence is known, as is shown in U.S. Pat. No. 3,959,081 which describes the use of chemiluminescence in the identification of bacteria. As with the transformer oils described above, it is found that each microorganism exhibits a characteristic time curve. Chemiluminescence has not however, been used in detection of alkaline-acid end point.

In the method of this invention, the intensity of light emission by the chemiluminescent indicator is monitored during the titration, and the first derivative of the light emission intensity is taken in order that the maximum of the light emission intensity (corresponding to the end-point) can be detected.

In accordance with a second aspect of the invention there is provided apparatus for carrying out the method of the first aspect of this invention, said apparatus comprising a vessel into which the chemiluminescent indicator and the sample of material to be analysed may be placed, means for feeding titrant at a constant rate into the vessel, a light detector for detecting the intensity of light emission by the indicator, a differentiating circuit for obtaining the first derivative with respect to time of the output signal of said light detector and a comparator circuit for providing an output signal indicative of when the first derivative of the output signal of said light detector reaches said amplitude level.

Preferably the vessel is light tight, in order to obtain maximum sensitivity. Preferably also, the internal surface of the vessel is covered by a reflective layer, for example of aluminium or silver, in order to reflect as much light as possible into the light detector, again to increase sensitivity.

Since the end-point of the titration reaction is determined by instrumental response only, without direct measurement of pH, it is necessary to calibrate the apparatus using oils having standard additions of acid at levels comparable with concentrations normally found in real oil samples. A calibration curve may then be drawn relating titrant volume against standard acid addition.

In order that the invention may be better understood, an embodiment thereof will now be described by way of example only and with reference to the accompanying drawings in which:

FIG. 3 is a series of graphs showing the waveforms in various parts of the circuit of FIG. 2.

Figure 1:
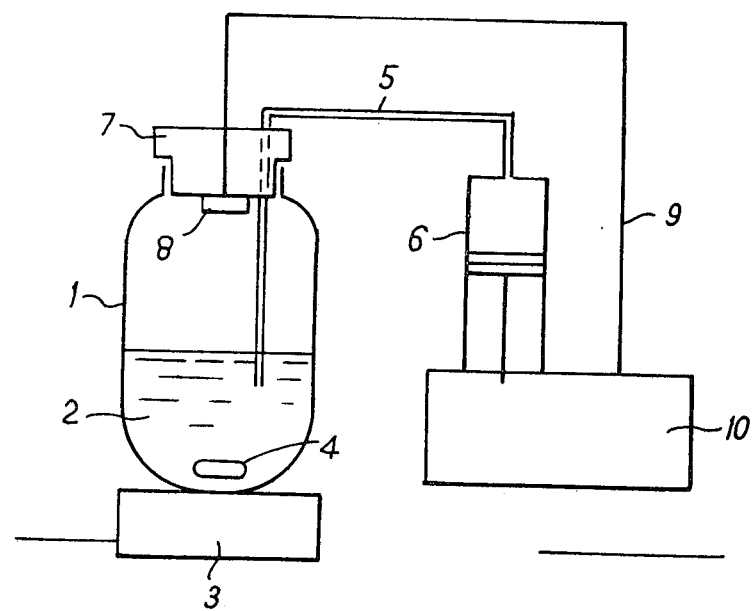
FIG. 1 is a diagrammatic view of a titrator incorporating one embodiment of the present invention.

Referring to FIG. 1, the titrator comprises a photometric titration vessel 1 which is light tight, in which the sample to be tested (suitably solubilised or dispersed in inert solvent) together with a quantity of a chemiluminescent indicator and hydrogen peroxide (shown collectively under reference 2) are placed. Mixing of the contents 2 is achieved by a magnetic stirrer 3 and a teflon covered spinning bar 4. During titration, titrant is gradually and continuously added to the contents of the vessel 1 via a small diameter polyethylene tube 5 from a constant flow burette 6.

The lid 7 of the vessel 1 is equipped with an integrated amplifier-photodetector 8, the output signal of which is passed via lead 9 to a detection system 10.

Figure 2:
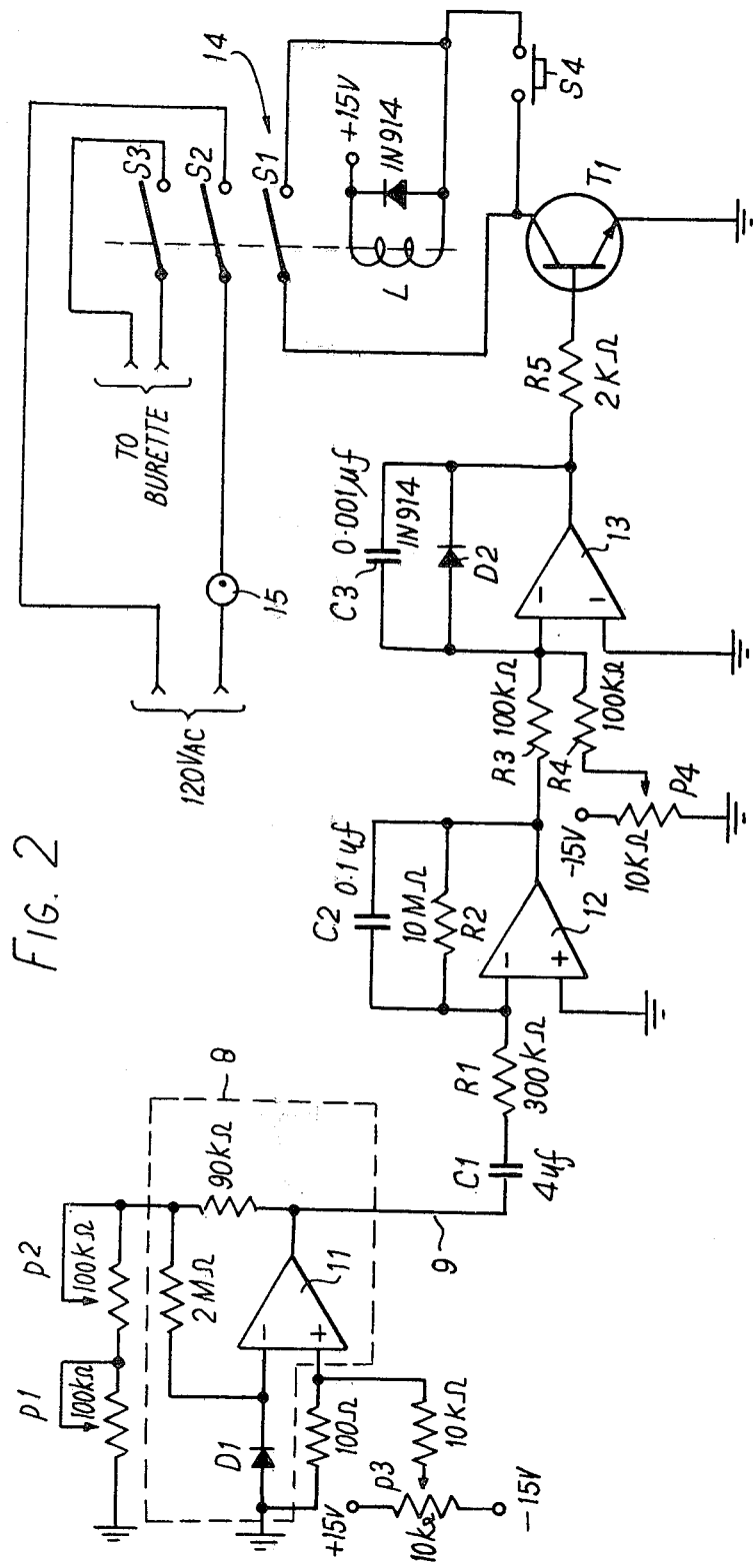
FIG. 2 is a circuit diagram of the detection system for use with the titrator of FIG. 1.

Referring now to FIG. 2, there is shown a circuit diagram of the electronic circuit of the detection system 10. Also shown in FIG. 2 is the circuit of the integrated amplifier-photodetector 8, manufactured by Bell-Howell under type number 509. This latter device comprises a photodiode D1 which is positioned to receive light emitted by the chemiluminescent indicator and an amplifier 11, both mounted within a single integrated circuit package. External potentiometers P1 and P2 control the fine and coarse gain respectively of the amplifier 11, while a third external potentiometer P3 is the offset adjustment for the same amplifier. The sensitivity of the amplifier-photodetector 8 is controlled by the potentiometers P1 and P2 in order to accommodate various kinds of sample, the output of amplifier 11 always being kept within the range 0–5 volts.

The output signal of the photodiode D1, amplified by amplifier 11, is passed along lead 9 to a conventional differentiating circuit comprising an amplifier 12, resistors R1, R2 and capacitors C1, C2. An example of the signal passed along lead 9 is shown in graph A of FIG. 3, and is typical for an oil sample containing a weak acid. Time $t=0$ represents the start of titration, when titrant begins to be added to the contents 2 of the vessel 1. As the titration proceeds, the light emission intensity of the chemiluminescent indicator, as represented by the amplified output signal of the photo-diode D1, gradually increases to a maximum, and then falls away. The maximum of the curve represents the end point of the titration reaction.

The differentiating circuit obtains the first derivative, with respect to titration time, of the amplified output signal of the photodiode D1, and produces an output signal as shown in graph B of FIG. 3 in which the central zero-crossing of the signal represents the end point of the titration reaction. The output signal of the differentiating circuit is passed to a zero-crossing detector comprising an amplifier 13, resistors R3, R4, potentiometer P4, diode D2 and capacitor C3.

The zero-crossing detector in fact comprises a d.c. level shifter and a voltage comparator.

The effect of the high-value resistors R3, R4 and the potentiometer P4 is to shift the d.c. level of the output signal of the differentiating circuit in a negative direction by an amount which is selectable between 0 and 15 volts by adjustment of potentiometer P4. The signal applied to the inverting input of amplifier 13 is thus d.c. shifted in a negative direction, as shown in graph C of FIG. 3. The amount of this d.c. level shifting is adjusted by potentiometer P4 to the minimum value that will ensure a sharp reproducible "instrument end-point", as represented by the right hand vertical dotted line in FIG. 3. For transformer oil, a typical value of level shifting is −0.15 volt.

The purpose of the "instrument end-point" is to ensure that the instrument is not switched off until after the actual end point, in order to ensure that a genuine maximum has occurred, and not just a transitory perturbation. The zero-crossing method used has been found sensitive to noise, and the d.c. level shift is effectively a protection chosen against the average noise output of the amplifier.

The d.c. level shift also serves to eliminate false starts, particularly when the sample is highly acidic. At the beginning of the titration, there is no light output and the differentiator output should therefore remain at zero. However, due to imperfect mixing, small flashes of light do occur during the beginning of the titration and unless these ripples, when amplified by the circuit, are below the cut-off voltage, it may be necessary to maintain the start contact 54 in its closed position until the proper light emission starts. Lowering the cut-off voltage eliminates this problem. This results in a constant known "error" factor which can be automatically compensated for during calculations.

The output signal of the amplier 13 is shown in graph D of FIG. 3, where the inverted output signal has been squared off by the action of the diode D12. This output signal is passed via an isolating resistor R5 to the base electrode of a transistor T1, for example type 2N3405. The transistor T1 is operated in switching mode, and controls the supply of current through the coil L of a relay 14.

The relay 14 is equipped with three normally open contacts S1, S2 and S3. The contacts S1 connect the end of the relay coil L remote from the supply to the collector of transistor T1. A normally open push-bottom switch S4 is connected in parallel with contacts S1 for a purpose to be described hereinafter. The contacts S2 are connected in series with a mains operated neon 15 which provides visual indication of the progress of titration. The contacts S3 switch power to operate the burette 6.

After the contents 2 have been added to vessel 1 and lid 7 placed on the titration chamber, the titration is started at time t=0 by momentarily closing the switch S4. This has the effect of driving current through the relay, via the transistor T1, which is hard on, and closing the three contacts S1, S2 and S3. Operation of the burette is thus initiated and the neon 15 is energised to indicate that the titration is proceeding. The relay is held on by the now closed contacts S1 which maintain current through the relay coil L. The condition of contacts S3 are shown in graph E of FIG. 3.

Before the during titration, the transistor T1 is switched hard on by the application to its base of a large positive bias—see graph D of FIG. 3. However, as soon as the instrument end-point is detected, the transistor T1 is switched off by the application of a negative voltage of −0.6 volts to its base. Current through the relay coil is thus stopped, and the relay contacts S1, S2 and S3 open, thus extinguishing the neon 15 and halting operation of the burette 6. When the base voltage of transistor T1 (as shown in graph D of FIG. 3) returns to its high positive level, the transistor T1 is again switched hard on. However, the relay contacts remain in their open position until the switch S4 is again closed—hence titration can not restart until switch S4 is manually closed.

Having isolated the end-point of the titration, it is only necessary to record the time taken for titration or the volume of titrant added, up to the end point, to be able to calculate using known techniques, the acid number level of the sample (see Example below).

There has thus been described an automatic photometric titrator using a technique which is simple, cheap and reliable, gives high sensitivity, and which furthermore does not require any direct contact between the sample being analysed and the detection system. The results obtained are comparable with those obtained by a standard potentiometric method (ASTM), but it is a much quicker method. A comparison obtained during routine usage on transformer oils and covering a range of acidity levels is as follows:

| Sample No. | mg KOH per gm of oil | |
|---|---|---|
| | By Standard Method | By Photometric Titrator |
| 1 | 0.17 | 0.17 |
| 2 | 0.10 | 0.09 |
| 3 | 0.02 | 0.02 |
| 4 | 0.32 | 0.33 |

The field of use of the invention is wide and has been used to test many different kinds of oils, for example lubricants, vegetable oils, fat, grease, mineral oil, and has also been used successfully with minor modifications for the analysis of milk and tomato juice.

EXAMPLE

Determination of acid number in black and dark oils.
Reagents:
  Hydrogen peroxide 15% Dilute 30% $H_2O_2$ with an equal volume of methanol.
  Solvent Mix one volume of toluene with one volume of isopropanol.
  Indicator: Solution of 0.2% lucigenin in methanol.
  Titrant KOH: 0.05 N solution in isopropanol. Standardized with potassium acid phthalate, with phenolphthalin as indicator.
Apparatus:
  Radiometer Autoburette type ABU13: Delivery speed: 1.5 ml/min. Photometric titration set up with automatic detection and stopping system.
Procedure:
  Weigh 10.0 g of oil to be analysed. Dilute in the titration vessel with 100 ml of the solvent. Add 2 ml each of the indicator and of the 15% hydrogen peroxide solution.
  Mix. Close the titration vessel. Start titrating. Wait for the automatic ending of the titration (approximately 1 minute).
  Note the total volume of the oil titration. Subtract the volume for the blank analysis.
Total Acidity number of oil sample =

$$\frac{(A - B)N \times 56.1}{\text{Weight of Sample}} = \frac{\text{mg KOH}}{\text{g oil}}$$

where:
A = volume of titrant (ml KOH) added during analysis of sample
B = volume of titrant (ml KOH) added during blank analysis
N = Normality of titrant KOH

I claim:
1. A method for detection of end-point in acid-base titration reactions to determine acid in an acid-containing material, said method comprising placing a quantity of a chemiluminescent indicator together with a sample of the acid-containing material to be analyzed into a vessel, gradually adding a suitable basic titrant to the vessel whilst monitoring by means of a light detector the intensity of light emission from the indicator, obtaining the first derivative with respect to time of the output signal of the light detector and detecting when the first derivative of the output signal reaches an amplitude level indicative of the acid-base reaction end-point.

2. A method as claimed in claim 1 wherein the light produced by the chemiluminescent indicator increases in a manner characteristic of the particular nature of the acid content of the material being analyzed as the acid level falls, reaches a maximum corresponding to the end point of the reaction, and then falls away as the solution becomes basic, so that the first derivative of the light detector output signal crosses zero at the point where the light output from the detector reaches its maximum.

3. A method as claimed in claim 2 wherein the d.c. level of the first derivative of the light detector output signal is shifted prior to detection of the zero-crossing point of the signal, in such a way that the end point of the reaction, is indicated as being slightly after the actual end point.

4. A method as claimed in claim 1 or 2 or 3, wherein the acid-containing material to be titrated is a dark or opaque oil or grease.

5. Apparatus for detecting end-point in titration to determine acid in acid-containing material by mixing a chemiluminescent indicator with the material, adding a basic titrant at a constant rate which is capable of causing light emission by the indicator and in accordance with said addition of titrant, and determining when the first derivative with respect to time, of change in said light emission, indicates that the light emission has reached a value indicative of said end-point, comprising a vessel into which the chemiluminescent indicator and the sample of material to be analyzed may be placed, means for feeding titrant at a constant rate into the vessel, a light detector for detecting the intensity of light emission by the indicator, a differentiating circuit for obtaining the first derivative with respect to time of the output signal of said light detector and a comparator circuit for providing an output signal indicative of when the first derivative of the output signal of said light detector has reached a level representing said end-point value.

6. Apparatus as claimed in claim 5 wherein the vessel is light tight.

7. Apparatus as claimed in either one of claims 5 or 6 wherein the vessel is lined internally with a light-reflective material.

8. Apparatus as claimed in claim 5 or 6 wherein the vessel is provided with means for agitating the contents.

9. Apparatus as claimed in claim 8 wherein the agitating means comprises a magnetic stirrer.

10. Apparatus as claimed in claim 5, wherein said comparator circuit comprises a zero-crossing detector.

11. Apparatus as claimed in claim 5 or 10, including means for shifting the d.c. level of the output signal of the differentiating circuit prior to its being passed to the comparator circuit.

12. Apparatus as claimed in claim 5 or 10 wherein the titrant feeding means comprises an electrically-operated burette which is connected so as to be switched on during the whole of the titration reaction, until the apparatus detects the end-point whereupon it is automatically switched off.

* * * * *

UNITED STATES PATENT AND TRADEMARK OFFICE
CERTIFICATE OF CORRECTION

PATENT NO. : 4,297,105
DATED : October 27, 1980
INVENTOR(S) : Ghyslain Dube

It is certified that error appears in the above–identified patent and that said Letters Patent are hereby corrected as shown below:

Col. 2, line 42 (in the equation), "(2)" should read -- -(2) -- .

Col. 5, line 52, before "during", "the" should read --and-- .

Signed and Sealed this

Ninth Day of November 1982

[SEAL]

Attest:

GERALD J. MOSSINGHOFF

Attesting Officer — Commissioner of Patents and Trademarks